United States Patent
Ramanathan et al.

(10) Patent No.: US 12,174,167 B2
(45) Date of Patent: Dec. 24, 2024

(54) MICROSTRUCTURALLY ENGINEERED PEROVSKITE GAS SENSOR

(71) Applicant: Purdue Research Foundation, West Lafayette, IN (US)

(72) Inventors: Shriram Ramanathan, West Lafayette, IN (US); Yifei Sun, Fujian (CN); Yoshitaka Sugita, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 290 days.

(21) Appl. No.: 17/802,099

(22) PCT Filed: Oct. 30, 2020

(86) PCT No.: PCT/US2020/058375
§ 371 (c)(1),
(2) Date: Aug. 24, 2022

(87) PCT Pub. No.: WO2021/173191
PCT Pub. Date: Sep. 2, 2021

(65) Prior Publication Data
US 2023/0085705 A1 Mar. 23, 2023

Related U.S. Application Data

(60) Provisional application No. 62/980,642, filed on Feb. 24, 2020.

(51) Int. Cl.
*G01N 33/00* (2006.01)
(52) U.S. Cl.
CPC .................. *G01N 33/005* (2013.01)

(58) Field of Classification Search
CPC .......................... G01N 27/125; G01N 33/005
See application file for complete search history.

(56) References Cited

U.S. PATENT DOCUMENTS

| | | | | |
|---|---|---|---|---|
| 4,314,996 A | * | 2/1982 | Sekido | G01N 27/4073 338/34 |
| 4,935,289 A | * | 6/1990 | Kikuchi | G01N 27/12 428/209 |
| 7,208,327 B2 | * | 4/2007 | Gstrein | G01N 27/129 438/10 |

(Continued)

FOREIGN PATENT DOCUMENTS

KR 101572032 B1 * 11/2015

OTHER PUBLICATIONS

"Correlated memory resistor in epitaxial NdNiO3 heterostructures with asymmetrical proton concentration" by Oh et al., Appl. Phys. Lett. 108, 122106 (2016) (Year: 2016).*

(Continued)

*Primary Examiner* — Justin N Olamit
(74) *Attorney, Agent, or Firm* — Purdue Research Foundation

(57) ABSTRACT

A gas sensing device is provided. The gas sensing device includes a substrate, a sensing film deposited on the substrate, and a plurality of electrodes deposited on the sensing film. The sensing film comprising ReNiO3, wherein Re is a rare-earth cation wherein. At least one of the electrodes including platinum, palladium, or a combination thereof. The electrodes are spaced apart from each other for measurement of electrical resistance.

18 Claims, 7 Drawing Sheets

(56) References Cited

U.S. PATENT DOCUMENTS

| | | | |
|---|---|---|---|
| 10,600,959 B2* | 3/2020 | Shi | H10N 70/8836 |
| 10,845,325 B2* | 11/2020 | Maboudian | G01N 27/4075 |
| 2002/0192852 A1 | 12/2002 | Scharf et al. | |
| 2005/0001721 A1 | 1/2005 | Houston et al. | |
| 2009/0181278 A1* | 7/2009 | Son | C25D 11/30 216/17 |
| 2013/0073239 A1 | 3/2013 | Edmondson | |
| 2015/0075254 A1 | 3/2015 | Sakuma et al. | |
| 2016/0091546 A1 | 3/2016 | Xia et al. | |
| 2016/0248006 A1 | 8/2016 | Shi et al. | |
| 2016/0377569 A1 | 12/2016 | Rajaraman et al. | |
| 2017/0309770 A1 | 10/2017 | Colli et al. | |
| 2020/0025966 A1* | 1/2020 | Ramanathan | G01V 3/088 |
| 2022/0259730 A1* | 8/2022 | Sønsteby | C23C 16/45555 |

OTHER PUBLICATIONS

International Search Report and Written Opinion issued by the ISA/US, Commissioner for Patents, mailed Feb. 5, 2021, for International Application No. PCT/US2020/058375; 10 pages.

Allen, S. J. et al., Gaps and psudogaps in perovskite rare earth nickelates, APL Mater. 3, 062503 (2015).

Gu, H. et al., Hydrogen Gas Sensors Based on Semiconductor Oxide Nanostructures. Sensors 2012, 12 (5), 5517-5550.

Ansari, S. et al., Grain Size Effects on H2 Gas Sensitivity of Thick Film Resistor Using SnO2 Nanoparticles. Thin Solid Films, 1997, 295 (1-2), 271-276.

Dey, A., Semiconductor Metal Oxide Gas Sensors: A Review. Materials Science and Engineering B 229, 2018, 206-217.

Zaghrioui, M. et al., Electron Diffraction and Raman Scattering Evidence of a Symmetry Breaking at the Metal-Insulator Transition of NdNiO3. Physical Review B, 2001, 64 (8), 081102.

Mengerink, K.J. et al., A call for deep-ocean stewardship. Science 44, 696-698 (2014).

Dowling, D.R. et al., Acoustic remote esnsing. Annu. Rev. Fluid Mech. 47, 221-243 (2015).

Kalmijn, A.J., Electric and magnetic field detection in elasmobranch fishes. Science 218, 916-918 (1982).

Bedore, C.N. et al., Bioelectric fields of marine organisms: voltage and frequence contributions to detectability by electroreceptive predators. Physiol. Biochem. Zool, 86, 298-311 (2013).

Shi, J. et al., Colossal resistance switching and band gap modulation in a perovskite nickelate by electron doping. Nat. Comm, 5, 4860 (2014).

Zhang, Z. et al., Perovskite nickelates as electric-field sensors in salt water. Nature, 553, 68 (2018).

* cited by examiner

MICROSTRUCTURALLY ENGINEERED PEROVSKITE GAS SENSOR

CROSS-REFERENCE TO RELATED APPLICATIONS

The present application is U.S. national stage entry under 35 U.S.C. § 371 of International Application No. PCT/US2020/058375, filed Oct. 30, 2020, which relates to and claims the priority benefit of U.S. Provisional Application No. 62/980,642, filed Feb. 24, 2020, the contents of which are hereby incorporated by reference in their entireties.

TECHNICAL FIELD

This disclosure relates to gas sensors and, in particular, to perovskite gas sensors.

BACKGROUND

Metal oxides are used as gas (e.g., $H_2$) sensor materials and the typical mechanism involves the reaction between the surface and chemisorbed gas molecule. However, for most of the oxide material systems, $H_2$ is not the only gas leading to such resistance evolution. Also, the limited resistance change upon $H_2$ intake still restricts low detection level (high sensitivity) of the sensor. It is because such reaction happens on the near-surface region of the oxide material only. Although many efforts have been endeavored to improve the performance of gas sensors, the maximum resistivity evolution range is still around 2-3 orders at elevated temperatures, limiting traditional hydrogen gas sensors to non-critical application such as a cylinder cabinet for stand-alone gas tank and handy alarm system to roughly check the existence of hydrogen.

BRIEF DESCRIPTION OF THE DRAWINGS

The embodiments may be better understood with reference to the following drawings and description. The components in the figures are not necessarily to scale. Moreover, in the figures, like-referenced numerals designate corresponding parts throughout the different views.

DETAILED DESCRIPTION

Figure 1:
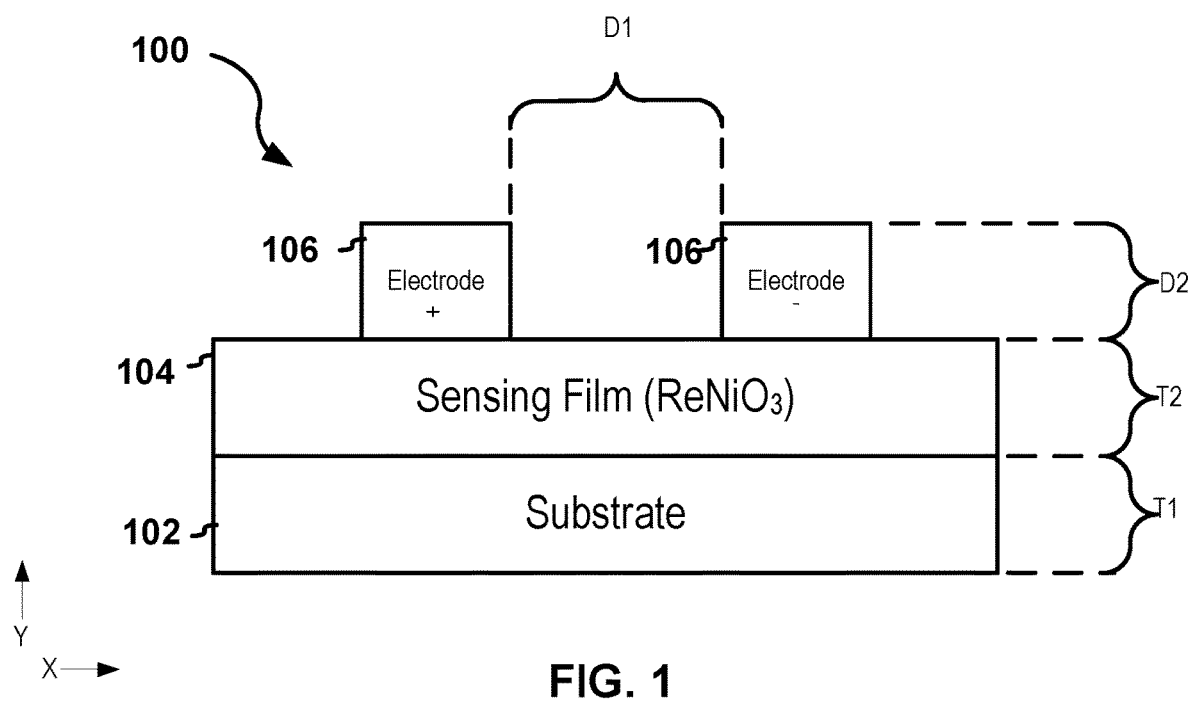
FIG. 1 illustrates a first example of a sensor device.

Metal oxides are used as gas (e.g., $H_2$) sensor materials and the typical mechanism involves the reaction between the surface and chemisorbed gas molecule. For example, the introduction of $H_2$ leads to the electrical resistance modification in inorganic oxide materials such as $SnO_2$ due to the change of the surface electron concentration. However, for most of the oxide material systems, $H_2$ is not the only gas leading to such resistance evolution. Also, the limited resistance change upon $H_2$ intake still restricts low detection level (high sensitivity) of the sensor. It is because such reaction happens on the near-surface region of the oxide material only. Although many efforts have been endeavored to improve the performance of gas sensors, the maximum resistivity evolution range is still around 2-3 orders at elevated temperatures, limiting traditional hydrogen gas sensors to non-critical application such as a cylinder cabinet for stand-alone gas tank and handy alarm system to roughly check the existence of hydrogen. Moreover, the selectivity and responsivity are still the bottlenecks for cost-effective and high performance $H_2$ sensing material.

Accordingly, a high performance perovskite sensor and manufacturing methods are provided. By way of introductory example, the sensor may include a substrate. A sensing film may be deposited on the substrate. A plurality of electrodes may be deposited on the sensing film. The sensing film may include $ReNiO_3$. The electrodes may be spaced apart from each other for measurement of electrical resistance. Re may include a rare-earth cation. At least one of the electrodes may include platinum, palladium, or a combination thereof.

In various examples, the substrate may between be 10 and 10000 micrometers thick. The sensing film may be between 10 nanometers and 1000 nanometers thick. The electrode is between 0.1 micrometer and 1 micrometer.

In various examples, the substrate may be etched to expose a surface of the sensing film on a side opposite to where the electrodes are positioned. The exposed surface of the sensing film may receive catalyst metal, which is porously applied. The dual side exposure to the environment can enhance the response of the sensing film.

In various examples, the electrodes may include at least two electrodes with different materials. A first electrode may include a catalyst metal, such as palladium or platinum. A second electrode may include an inert gas metal, such as gold, which is densely or porously applied. This asymmetric sensor device will enable one electrode to rapidly respond to the environment locally while the other electrode is used to measure the response in combination with the catalytic electrode.

A technical advantage provided by the sensor device 100 and methods described herein is that $ReNiO_3$ materials (where Re is a rare-earth cation such as Sm, Nd, Eu, Pr, La, etc) provide a high performance gas sensor for $H_2$ and else. The Ni-centered octahedral structure in a perovskite lattice across the whole film thickness may be considered as reaction sites with $H_2$. Alternative or in addition, films in either crystalline or amorphous phase may provide an effective gas sensor material, especially which results in the colossal resistance greater than five orders of magnitude ($10^5$) upon $H_2$ intake for the crystalline films. Also, film crystalline structural engineering may effectively improve the hydrogen selectivity and sensitivity, particularly with the $ReNiO_3$ oxide materials family.

Additional and alternative benefits, efficiencies, and improvements are made evident in the sensor and methods described below.

FIG. 1 illustrates a first example of a gas sensor device 100. The sensor device 100 may include a substrate 102, a sensing film 104 deposited on the substrate 102, and electrode(s) 106 deposited on the sensing film 104. The electrodes may be positioned on a first side of the sensor whereas the substrate may be positioned on a second side of the sensor opposite the first side, with respective to a Y direction. The first side is also herein referred to as the "top side." The second side is also herein referred to as the "bottom side". The substrate or combination of sensing film and substrate may follow a plane orthogonal to the Y direction (i.e. an x-z plane).

In various examples, the substrate 102 may include a single crystalline or plastic based substrate 102. For example, the substrate 102 may include lanthanum aluminum (LAO) oxide or polyethylene terephthalate (PET). In some examples, the substrate 102 may have a thickness (T1) of between 10 and 20000 micrometers.

The sensing film 104 may include $ReNiO_3$. Re may refer to a rare-earth cation. For example, the sensing film 104 may be a $NdNiO_3$ film and/or a $SmNiO_3$ film. The sensing film 104 may be porous and/or dense. In porous examples, the sensor film may include pores with a pore size between 5 and 1000 nanometers. In dense example, the sensor film may have pores with a pore size less than 5 nanometers. The sensing film 104 may have a thickness (T2) between 10 nanometers and 1000 nanometers.

The sensing film 104 may be applied to the substrate 102 with a deposition technology. The deposition technology may include, for example, physical vapor deposition (PVD) and/or pulsed laser deposition (PLD). Alternatively, the deposition technology may include chemical deposition techniques such as atomic layer deposition (ALD), spray casting, chemical vapor deposition, etc.

In various examples, the electrodes 106 may include, platinum, palladium, or other suitable metal. The electrodes 106 may be deposited on the sensing film 104 with, for example, electron beam evaporation, sputtering or some other suitable technology. The electrodes 106 may have a thickness (T3) between 0.1 micrometer and 1 micrometer. The electrodes 106 may be spaced apart by a distance (D1) between 50 micrometers to 10000.

Figure 2:
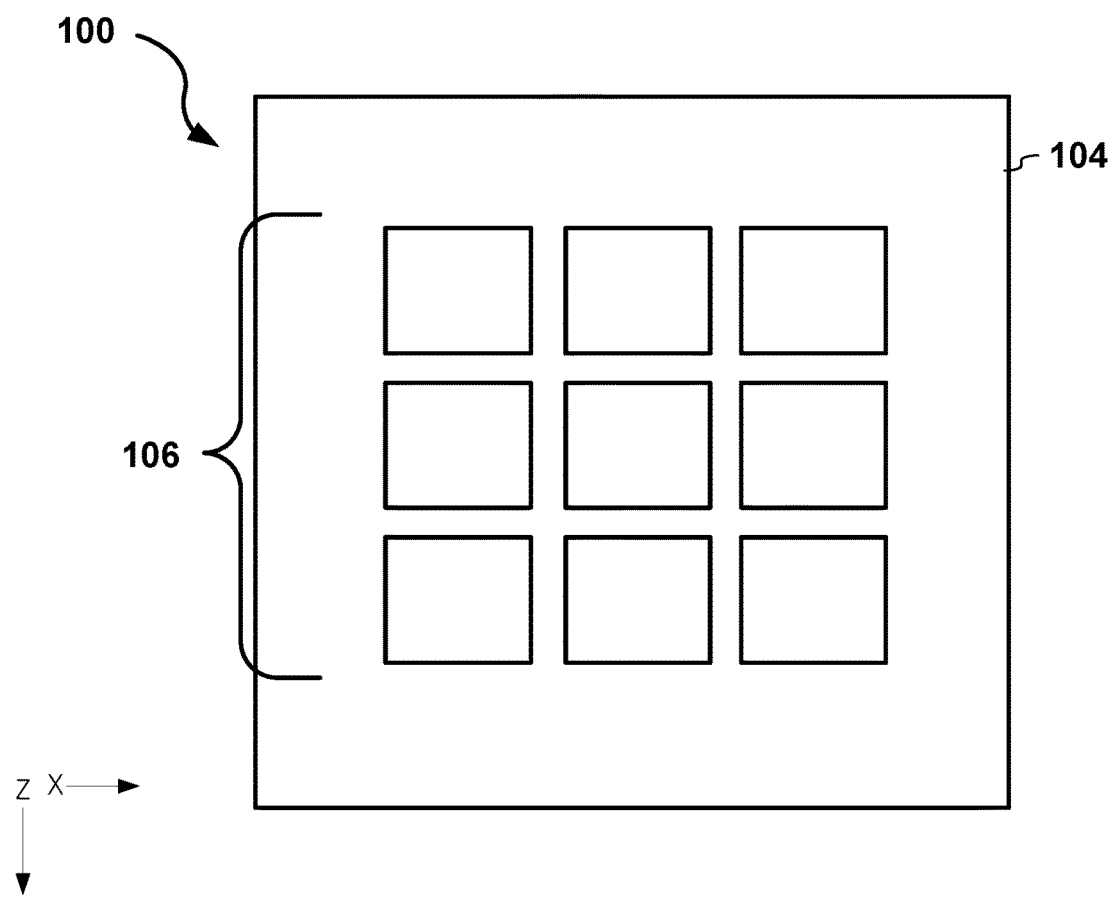
FIG. 2 illustrates a second example of a sensor device.

FIG. 2 illustrates a second example of the sensor device 100. As illustrates in FIG. 2, the sensor device 100 may include a plurality of electrodes 106 arranged in a pattern. The electrodes 106 may be placed on the sensing film 104 according to a uniform (as shown in FIG. 2) or non-uniform pattern.

Figure 3:
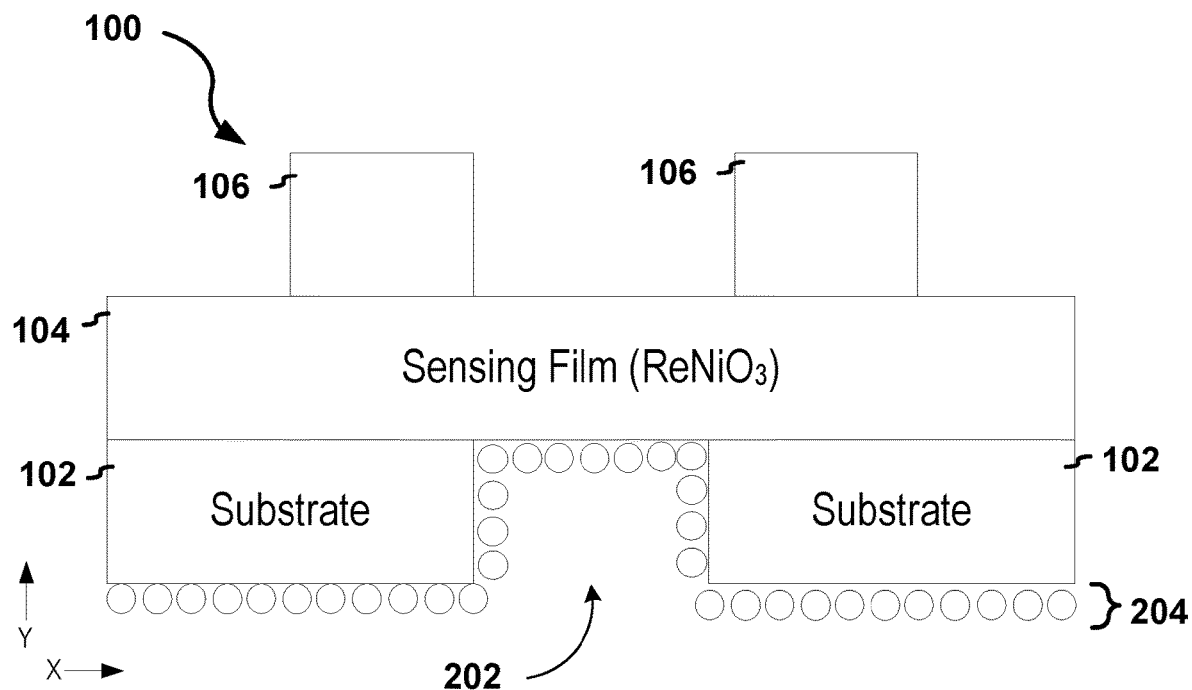
FIG. 3 illustrates a third example of a sensor device.

FIG. 3 illustrates a third example of the sensor device 100. The sensor device can be fabricated with thin film rare-earth nickelate film grown on a substrate such as silicone, glass, LaAlO3 or other single crystal template. Following film deposition, the electrodes 106, such as platinum, palladium or their combination may be deposited on the film to measure the electrical properties. The substrate may be etched chemically using chemical reagents or by dry etching using an ion mill to create exposed film region 202 on the bottom side. The exposed film region may be defined by a recess formed substrate during the chemical or dry etching process. A porous catalytic metal such as platinum or palladium may be deposited on the backside (the side opposite the sensor side) to form a porous catalytic metal deposition 204. The porous catalytic metal deposition may extend along substrate and sensing film on the back side. The dual side exposure to the environment provides a technical advantage of enhancing the response of the sensing media. While the electrodes on the top side of the sensor are for measuring the change in resistance due to H2 or gas sensing the porous metal on the bottom side increases catalytic sites for H2 or other gas atom intercalation to enhance sensing metrics. The pore size for the porous catalytic metal deposition 204 can be from few nanometers to few micrometers.

Figure 4:
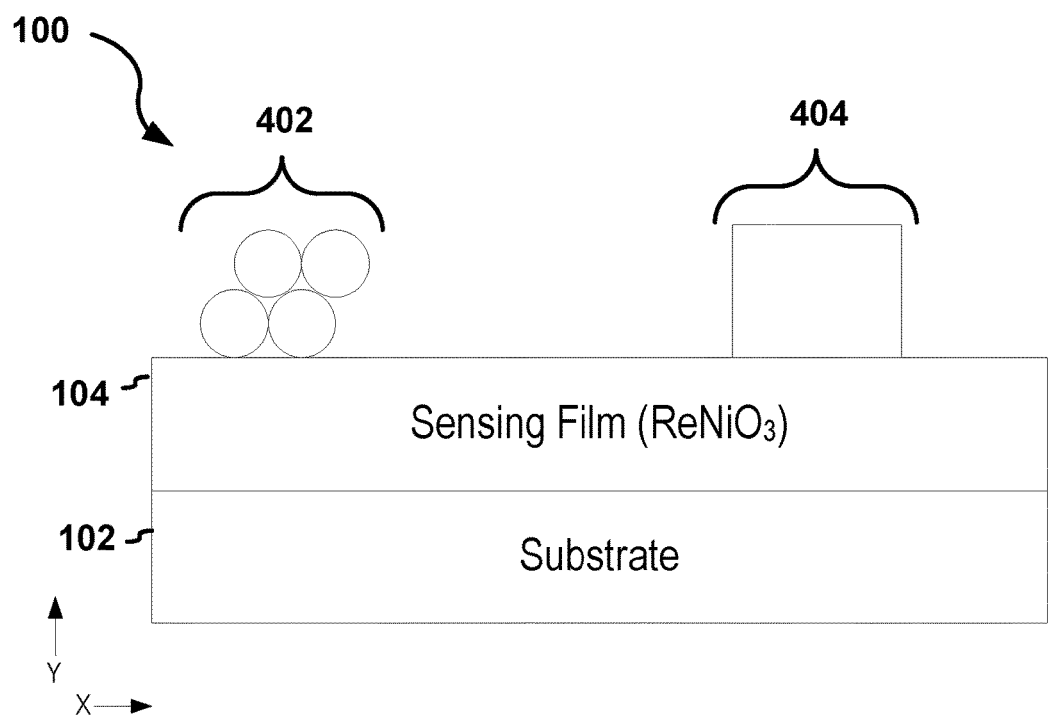
FIG. 4 illustrates a fourth example of a sensor device.

FIG. 4 illustrates a fourth example of the sensor device 100. At least two of the electrodes may include different corresponding materials. For example, the electrodes include a first and second electrode 402, 404. The first electrode 402 may include a porous and catalytic material such as Pt, Pd or their combination. The second electrode 404 may include material that is both dense and inert, such as gold. The first 402 (the catalytic electrode) may respond to the gas and enhance adsorption of gas molecule at the electrode-sensing film boundary. The first electrode 402 (catalytic electrode) will catalyze the decomposition of sensed gas (such as H2 or else) and the decomposed gas will lead to the resistance change of sensing film 104. The second electrode 404 remains unaffected and provides a counter-electrode to measure the resistance change upon gas exposure. Accordingly the sensor device 100 will enable the first electrode 402 (catalytic electrode) to rapidly respond to the environment locally while the second electrode 404 is used to measure the response in combination with the catalytic electrode.

Figure 5:
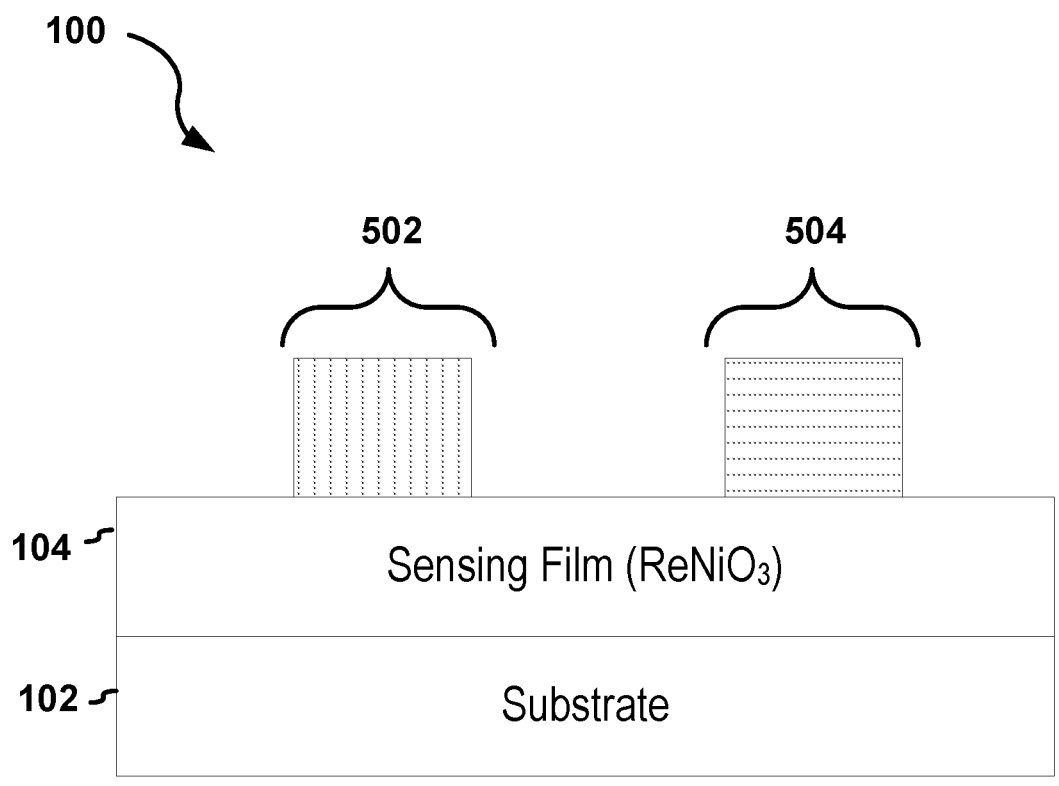
FIG. 5 illustrates a fifth example of a sensor device.

FIG. 5 illustrates a fifth example of the sensor device 100. Like the example in FIG. 4, at least two of the electrodes 502, 504 include different corresponding materials. However, in this example, the first electrode 502 (having the catalytic material) may be dense instead of porous. While the porous electrode may include a film may having a pore size than can vary from a few nanometers to a few micrometers (based on deposition conditions), the dense electrode may include a film with no fully covering whatever surface it is on. Thus, the porous catalytic electrode may allow gas molecules to access the layer underneath, therefore increasing surface area for catalytic action and increasing sensing performance.

By depositing multiple electrodes on the surface each of which is catalytic to different gases/chemical molecules along with an inert counterelectrode, an array of sensor devices can be fabricated on a single chip to sense multiple species.

The sensor device 100 may be implemented with additional, different, or fewer components than illustrated. Each component may include additional, different, or fewer components. The appendix provides additional and alternative examples, benefits, and methods.

Experimental Results

In an experiment, a crystal $NdNiO_3$ (NNO) thin films grown on lanthanum aluminum oxide (LAO) substrates were prepared using magnetron sputtering technology at room temperature combined with post-annealing in air atmosphere. Here, the deposition technology utilized was magnetron sputtering but could also be other physical vapor deposition (PVD) technologies including pulsed laser deposition (PLD), chemical deposition techniques such as atomic layer deposition (ALD), spray casting, etc. The deposition condition for NNO film was typically 20 vol % of $O_2$ with Ar balanced at a background pressure of 1.5-50 mTorr from $NdNiO_3$ ceramic target. Applied RF power was 150-250 W. The deposition rate was 10-40 nm per hour. The as-deposited samples were annealed in open air at 500° C. for 24 h in a tube furnace. Patterned platinum electrode were deposited on NNO thin film by Electron beam-evapolation system to give 100 nm of thickness.

Various kinds transition metal oxide thin films could be used (e.g. SmNiO3, or other systems such as ReNiO3 where Re is a rare-earth cation such as Nd, Eu, Pr, La etc or rare-earth oxide alloy combinations such as $(Sm_xNd_{1-x})NiO_3$ where x can vary between 0 and 1. Binary oxides such as NiO and alloy oxides such as Re2O3-NiO where Re is a rare-earth cation may also be used by deposition at room temperature.) Films were also deposited on a commercial Polyethylene terephthalate (PET) substrate without post-annealing. The thickness of the substrate could vary from 0.1 mm to 2 mm. In a typical process, metallic targets of Sm and Ni for deposition were used. The power for Sm target was 170 w and the power to Ni target was 85 W. Substrate temperature may vary from liquid nitrogen temperature (77K) to about 200° C., within the stability range for PET substrate. The deposition background pressure is 5 mTorr and the deposition gas composition is 40 sccm Ar and 10 sccm $O_2$. The deposition rate is 140 nm per hour. The film used was 50 nm. But the thickness could range from 10 nm to 1000 nm.

Figure 6:
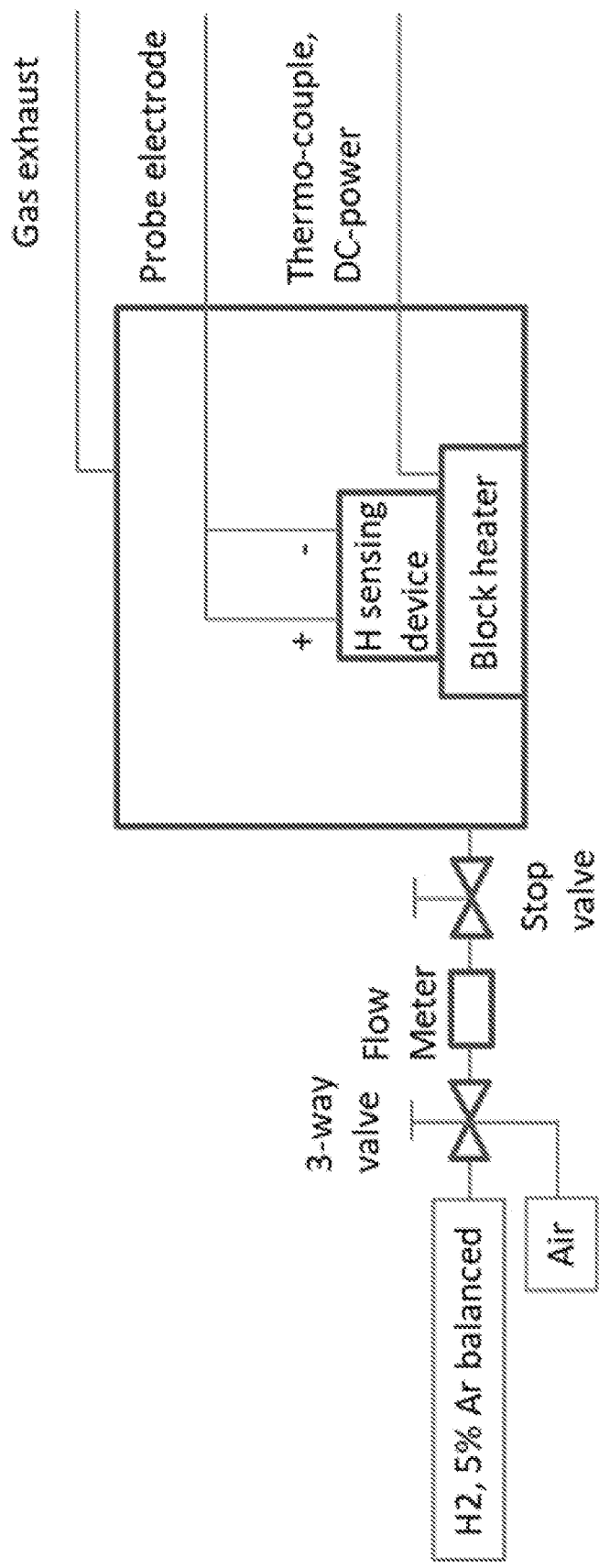
FIG. 6 shows an example of an experimental setup for a sensor device.

FIG. 6 shows an example of an experimental setup for the sensor device 100. 5 vol % (Ar-balanced) of $H_2$ was introduced into stainless-steel chamber at a flow rate of 150 sccm to investigate hydrogen sensitivity of NNO film which was kept at 100° C. and SNO film which was kept at 50° C. The voltage applied range was −0.1 to 0.1 V at a step of 0.02 V in 0.01 sec between two finger electrodes deposited on film. For O3 sensing measurement, similar setup was used by replacing 5 vol % (Ar-balanced) with O3.

In a typical fabrication, an array of Pd electrode pattern was deposited onto the film by sputtering. The deposition condition for Pd was 5 mTorr in 40 Sccm Ar gas. The power to Pd target was 100 w which gave the growth rate of 100 nm per 5 min.

The detail of deposition parameters dependent NNO films performance as $H_2$ sensor is shown in Table 1. All five films were exposed to $H_2$ gas for prolonged measurement until the resistance reached plateau. As can be seen in the table, all films show high resistance change (>8 orders of magnitude) after $H_2$ intake, indicating the high sensitivity of the film.

TABLE 1

Summary of experiment for NNO

| No. | Deposition Pressure [mTorr] | Power of NNO target [W/inch$^2$] | Film Thickness [nm] | Resistance increase ratio |
|---|---|---|---|---|
| 1 | 50 | 12 | 52 | 7E8 |
| 2 | 10 | 12 | 40 | 1E9 |
| 3 | 50 | 20 | 40 | 5E8 |
| 4 | 1.5 | 16 | 84 | 4E8 |
| 5 | 1.5 | 20 | 110 | 2E8 |

Figure 7:
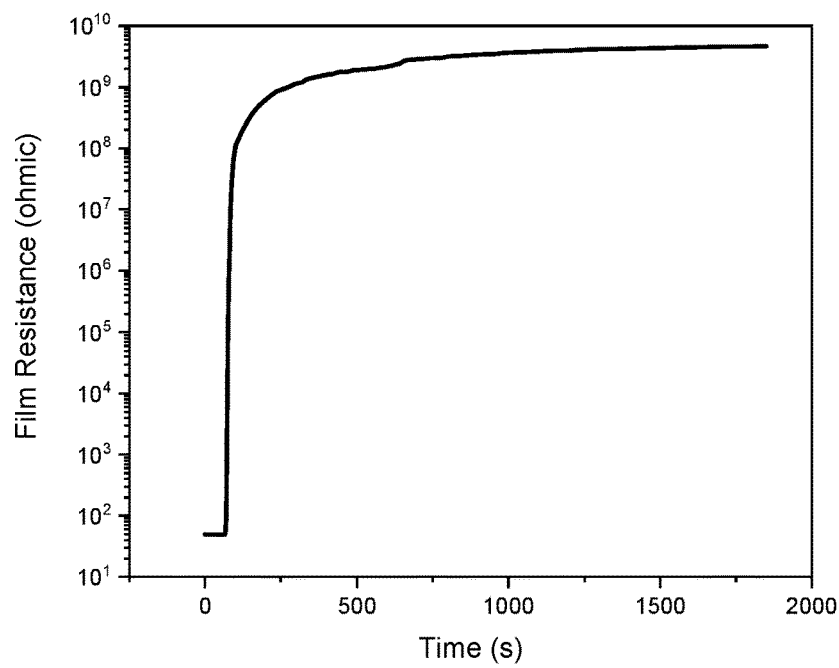
FIG. 7 illustrates a time dependent resistance evolution of NNO film in $H_2$ gas according to various experimental results.

FIG. 7 illustrates time dependent resistance evolution of NNO film in $H_2$ gas according to various experimental results. The data were collected at 25° C. Collected electrical resistance data were plotted by time course. One example of time dependent resistance evolution is shown in FIG. 7 (sample No. 2). A drastic increase is seen in initial few minutes, and final self-limited resistance value is obtained 1800 sec after introducing hydrogen to crystalline NNO film.

Figure 8:
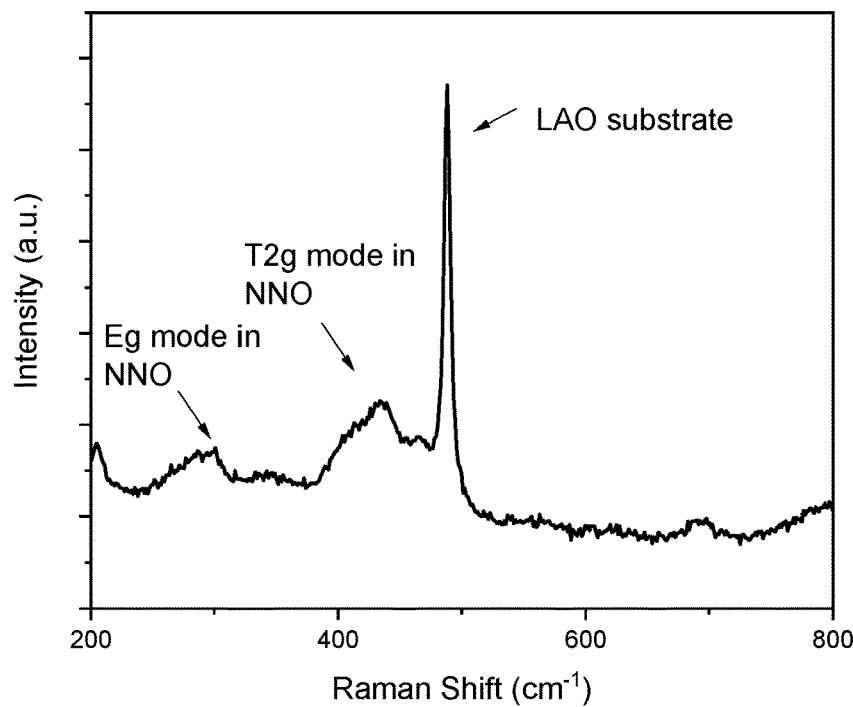
FIG. 8 illustrates Raman spectra for NNO film on LAO substrate according to various experimental results.
Figure 9:
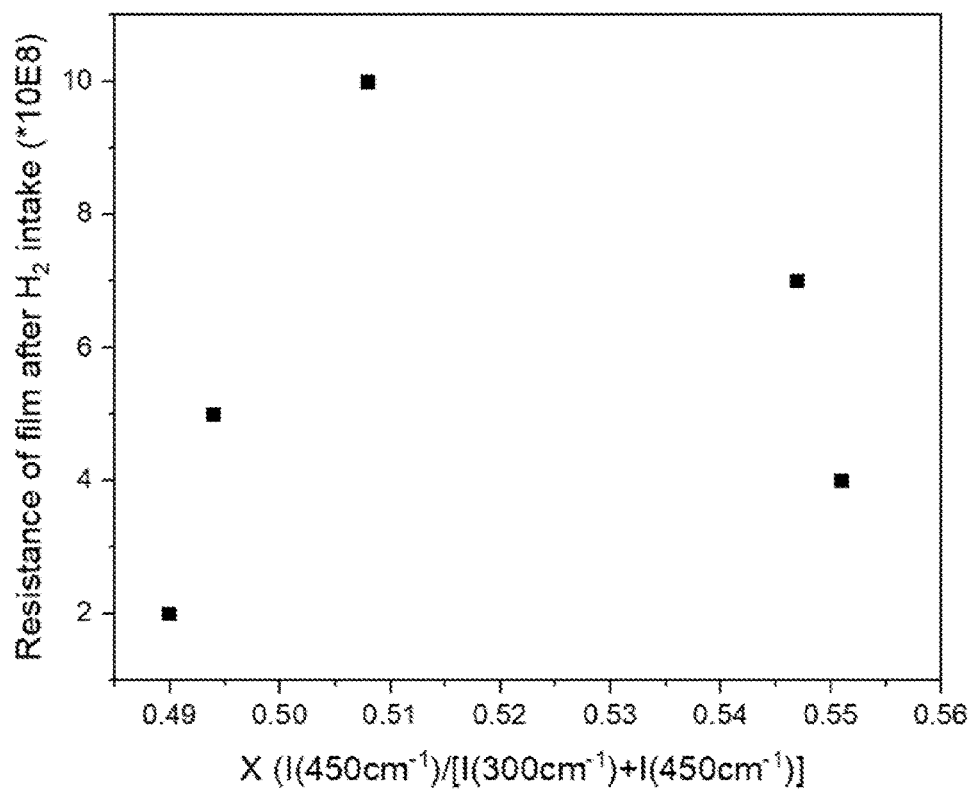
FIG. 9 illustrates Raman peak intensity dependent NNO Film resistance change upon $H_2$ intake according to various experimental results.

FIG. 8 illustrates Raman spectra for NNO film on LAO substrate according to various experimental results. FIG. 9 illustrates Raman peak intensity dependent NNO Film resistance change upon $H_2$ intake. The Raman spectra of NNO (sample No. 2) was conducted and displayed in FIG. 8. The Raman measurement was taken with a spectrometer from Renishaw using a 2400 tr/mm grating. The incident wavelength was the 532 nm laser magnified by ×50 lens with about 10 mW on the sample. Measurement was performed at room temperature. It can be observed that there are two strong peaks at 300 cm−1 and 450 cm−1 which are assigned as Eg and T2g vibration modes in crystalline perovskite, respectively (FIG. 8). And they can be considered as the internal modes of the free $NiO_6$ octahedron. This octahedral component is important for hydrogen acquisition, and its evolution causes drastic increase of electrical resistance after hydrogenation. The hydrogenation of NNO film results in the disappearance of $T_{2g}$ (450 cm$^{-1}$) peak. Therefore, here, we speculate that peak intensity (I) ratio (X)=I(450 cm$^{-1}$)/[I(300 cm$^{-1}$)+I(450 cm$^{-1}$)] could be a descriptor for hydrogen intake (FIG. 9). Remarkable R ratio increase can be seen with X from 0.48 to 0.56 as it is represented in FIG. 9.

Figure 10:
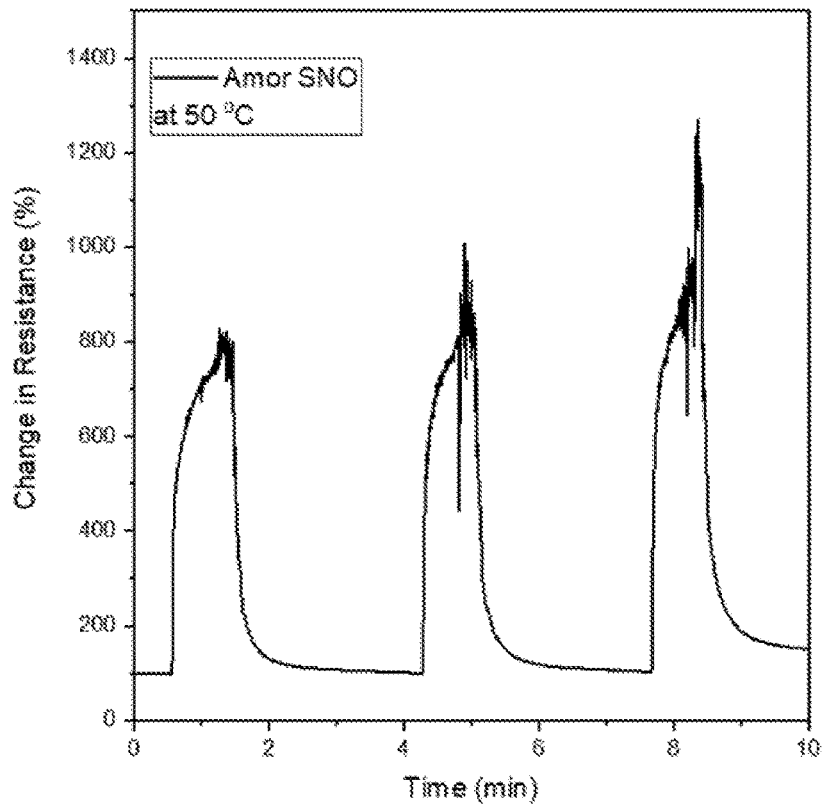
FIG. 10 illustrates gas sensing performance for $H_2$ of SNO film deposited on PET substrate without annealing according to various experimental results.

FIG. 10 illustrates gas sensing performance for $H_2$ of SNO film deposited on PET substrate without annealing according to various experiments. Besides the crystalline film, the gas sensing performance of SNO film deposited on PET without annealing is shown in FIG. 10. The gas environment was switching between $H_2$ and air. The hydrogenation time was 60 s and time exposed to air was 180 s. The device showed significant sensitivity toward $H_2$ with the increase of resistance by >800% during our measurement. After switching the gas back to open air. The resistance of the device quickly fell back to its pristine state. The cycling measurement indicates the good repeatability of the device. Change in the electronic structure of the sensing element due to hydrogen exposure allows high contrast measurements of the local environment. This result opens up the use of nickel oxide containing sensing materials to be fabricated on inexpensive polymer substrates.

Figure 11:
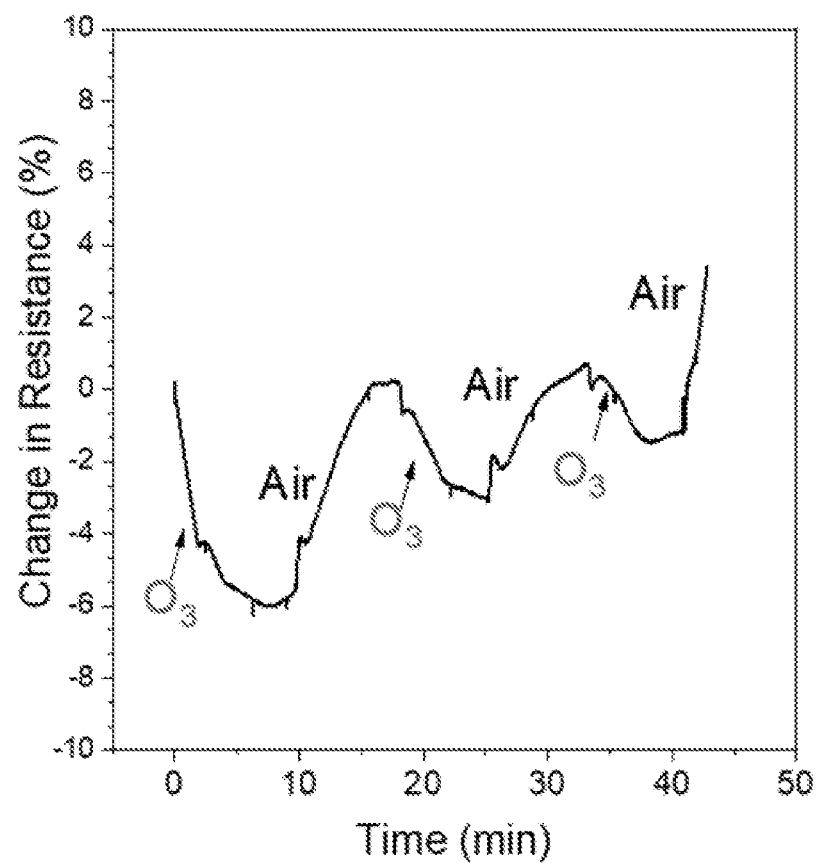
FIG. 11 illustrates gas sensing performance for $O_3$ of SNO film deposited on PET substrate without annealing according to various experimental results.

FIG. 11 illustrates gas sensing performance for $O_3$ of SNO film deposited on PET substrate without annealing according to various experiments. Besides to sensing of $H_2$, the gas sensing performance of ozone ($O_3$) was also conducted on our SNO film deposited on PET with annealing and shown in FIG. 11. Both $O_3$ time and airtime were 10 min. The testing temperature was 50° C. The device showed visible sensitivity toward $O_3$ with the decrease of resistance by ~5% during our measurement. After switching the gas back to air, the resistance of the device apparently increased. The cycling measurement also indicates the repeatability of the device. The different extent in resistance change to different gases suggests that arrays of such devices can be constructed to sense the chemical and gaseous environment in a variety of applications.

It should be appreciated that the experimental results described herein are demonstrative of the technical advancements that are possible by the sensor and related methods described herein, but are not intended to limit the all embodiments of the sensor or related methods. In practice, the actual results may vary, depending on which aspects of the sensor are selected and implemented to satisfy the design constraints that are specific to a particular application.

To clarify the use of and to hereby provide notice to the public, the phrases "at least one of <A>, <B>, . . . and <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

While various embodiments have been described, it will be apparent to those of ordinary skill in the art that many more embodiments and implementations are possible. Accordingly, the embodiments described herein are examples, not the only possible embodiments and implementations.

What is claimed is:

1. A gas sensor device comprising:
a substrate, a sensing film deposited on the substrate, and a plurality of electrodes deposited on the sensing film, the sensing film comprising ReNiO3, the electrodes spaced apart from each other for measurement of electrical resistance, wherein Re is a rare-earth cation wherein at least one of the electrodes comprise, platinum, palladium, or a combination thereof
wherein the electrodes are positioned on the sensing film on a first side of the gas sensor device, wherein the substrate is etched to define an exposed surface of the sensing film on the second side of the gas sensor device, wherein the gas sensor device further comprises a porous catalytic metal layer deposited on the exposed surface of the sensing film on the second side of the gas sensor device.

2. The sensor device of claim 1, wherein ReNiO3 is NdNiO3.

3. The sensor device of claim 1, wherein ReNiO3 is SmNiO3.

4. The sensor device of claim 1, wherein ReNiO3 is (SmxNd1-x) NiO3 or a combination of different rare-earth cations based oxide alloys.

5. The sensor device of claim 1, wherein the substrate comprises polyethylene terephthalate or lanthanum aluminum oxide.

6. The sensor device of claim 1, wherein the electrodes comprise a first electrode and a second electrode, the material of the first electrode different from the second electrode.

7. The sensor device of claim 6, wherein the material of the first electrode comprises platinum, palladium, or a combination thereof and the material of the second electrode comprises an inert metal.

8. The sensor device of claim 7, wherein the inert metal is gold.

9. The sensor of device 7, wherein a first electrode of the electrodes is porous, wherein the first electrode has a pore size between 2 nanometer and 100 nanometers.

10. The sensor device of claim 1, wherein the substrate has a thickness between 10 and 10000 micrometers.

11. The sensor device of claim 1, wherein the sensing film has a thickness between 10 nanometers and 1000 nanometers.

12. The sensor device of claim 1, wherein the electrode has a thickness between 0.1 micrometer and 1 micrometer.

13. The sensor device of claim 1, wherein the electrodes are spaced apart by a distance measuring 50 micrometers to 10000 micrometers.

14. The sensor device of claim 1, wherein the sensor film is annealed.

15. The sensor device of claim 1, wherein the sensor film is porous, the sensor film having pore size between 5 and 1000 nanometers.

16. The sensor device of claim 1, wherein the sensor film is dense, the sensor film having a pore size less than 5 nanometers.

17. The sensor device of claim 1, wherein the catalytic metal comprises platinum, palladium, or a combination thereof.

18. A method, comprising:
obtaining a substrate material;
depositing a sensing film on the substrate material with physical vapor deposition, the sensing film comprising ReNiO3, wherein Re is a rare-earth cation; and
depositing a plurality of electrodes on the sensing film;
annealing the sensor film on the substrate material;
etching the substrate material to expose a region of the sensing film; and
depositing a catalytic metal on the exposed region of the sensing film.

* * * * *